(12) United States Patent
Altarac et al.

(10) Patent No.: US 9,113,964 B2
(45) Date of Patent: *Aug. 25, 2015

(54) ANTERIOR CERVICAL PLATE

(71) Applicant: Howmedica Osteonics Corp., Mahwah, NJ (US)

(72) Inventors: Moti Altarac, Irvine, CA (US); Joey Reglos, Lake Forest, CA (US); John Fredrick Stephani, Soquel, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,458

(22) Filed: Aug. 6, 2014

(65) Prior Publication Data

US 2014/0350601 A1    Nov. 27, 2014

Related U.S. Application Data

(63) Continuation of application No. 14/158,995, filed on Jan. 20, 2014, which is a continuation of application No. 13/185,641, filed on Jul. 19, 2011, now Pat. No. 8,668,723.

(51) Int. Cl.
*A61B 17/80*    (2006.01)
*A61B 17/70*    (2006.01)
*A61B 17/86*    (2006.01)

(52) U.S. Cl.
CPC ......... *A61B 17/7059* (2013.01); *A61B 17/8042* (2013.01); *A61B 17/8047* (2013.01); *A61B 17/8605* (2013.01); *A61B 17/8615* (2013.01)

(58) Field of Classification Search
USPC ...................... 606/70–71, 280–299; 411/132, 411/134–136, 147–148, 102, 107, 999
See application file for complete search history.

(56) References Cited

U.S. PATENT DOCUMENTS

| 5,364,399 A | 11/1994 | Lowery et al. |
| 5,549,612 A | 8/1996 | Yapp et al. |
| 5,616,142 A | 4/1997 | Yuan et al. |
| 5,616,144 A | 4/1997 | Yapp et al. |
| 6,045,552 A | 4/2000 | Zucherman et al. |
| 6,139,550 A | 10/2000 | Michelson |

(Continued)

FOREIGN PATENT DOCUMENTS

| EP | 1520545 B1 | 11/2006 |
| EP | 1429675 B1 | 10/2007 |

(Continued)

*Primary Examiner* — Anu Ramana
*Assistant Examiner* — Jessica Weiss
(74) *Attorney, Agent, or Firm* — Lerner, David, Littenberg, Krumholz & Mentlik, LLP

(57) ABSTRACT

An anterior cervical plate system is provided. The cervical plate includes a retention ring with a deflectable flange that is upwardly spaced from the top surface of the ring and configured to prevent an inserted bone fastener from backing out of the plate. The plate includes a locking pin having a camming surface and a blocking surface. When the camming surface is moved into position adjacent to the flange, the flange is free to flex out of the way of a bone screw being inserted into or removed from the plate. When the blocking surface is positioned adjacent to the flange, outward deflection of the flange is prevented to retain the bone screw inside the plate. The locking pin is rotated through a camming surface to bring a blocking surface against the flange deflecting the flange onto the head of the bone screw.

27 Claims, 15 Drawing Sheets

(56) References Cited

U.S. PATENT DOCUMENTS

| | | |
|---|---|---|
| 6,258,089 B1 | 7/2001 | Campbell et al. |
| 6,261,291 B1 | 7/2001 | Talaber et al. |
| 6,398,783 B1 | 6/2002 | Michelson |
| 6,599,290 B2 | 7/2003 | Bailey et al. |
| 6,602,255 B1 | 8/2003 | Campbell et al. |
| 6,605,090 B1 | 8/2003 | Trieu et al. |
| 6,626,907 B2 | 9/2003 | Campbell et al. |
| 6,629,998 B1 | 10/2003 | Lin |
| 6,652,525 B1 | 11/2003 | Assaker et al. |
| 6,695,846 B2 | 2/2004 | Richelsoph et al. |
| 6,743,256 B2 | 6/2004 | Mason |
| 6,755,833 B1 | 6/2004 | Paul et al. |
| 6,793,658 B2 | 9/2004 | LeHuec et al. |
| 6,964,664 B2 | 11/2005 | Freid et al. |
| 7,008,426 B2 | 3/2006 | Paul |
| 7,070,599 B2 | 7/2006 | Paul |
| 7,175,623 B2 | 2/2007 | Thramann et al. |
| 7,186,254 B2 | 3/2007 | Dinh et al. |
| 7,204,837 B2 | 4/2007 | Paul |
| 7,220,263 B2 | 5/2007 | Cordaro |
| 7,255,699 B2 | 8/2007 | Paul |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,322,984 B2 | 1/2008 | Doubler et al. |
| 7,438,715 B2 | 10/2008 | Doubler et al. |
| 7,452,370 B2 | 11/2008 | Anderson |
| 7,468,069 B2 | 12/2008 | Baynham et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,662,174 B2 | 2/2010 | Doubler et al. |
| 7,686,806 B2 | 3/2010 | Rhyne |
| 7,740,630 B2 | 6/2010 | Michelson |
| 7,740,649 B2 | 6/2010 | Mosca et al. |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,857,839 B2 | 12/2010 | Duong et al. |
| 7,887,547 B2 | 2/2011 | Campbell et al. |
| 7,909,859 B2 | 3/2011 | Mosca et al. |
| 7,963,981 B2 | 6/2011 | Binder et al. |
| 7,985,242 B2 | 7/2011 | Forton et al. |
| 8,057,522 B2 | 11/2011 | Rothman et al. |
| RE43,008 E | 12/2011 | Talaber et al. |
| 8,128,668 B2 | 3/2012 | Paul |
| 8,221,476 B2 | 7/2012 | Paul |
| 8,236,033 B2 | 8/2012 | Paul |
| 8,236,034 B2 | 8/2012 | Binder et al. |
| 8,419,777 B2 | 4/2013 | Walker et al. |
| 8,562,655 B2 | 10/2013 | Butler |
| 8,562,656 B2 | 10/2013 | Humphreys |
| 8,591,556 B2 | 11/2013 | Hansell et al. |
| 8,668,723 B2 | 3/2014 | Altarac et al. |
| 2002/0120270 A1 | 8/2002 | Trieu et al. |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187551 A1 | 8/2005 | Orbay et al. |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |

(56) References Cited

U.S. PATENT DOCUMENTS

| | | |
|---|---|---|
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0042159 A1 | 2/2010 | Butler |
| 2010/0049256 A1 | 2/2010 | Jeon et al. |
| 2010/0069968 A1 | 3/2010 | Assaker et al. |
| 2010/0234897 A1 | 9/2010 | Fisher et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0213421 A1 | 9/2011 | Binder et al. |
| 2011/0270311 A1 | 11/2011 | Assaker et al. |
| 2013/0184767 A1 | 7/2013 | Kaufman et al. |
| 2013/0197588 A1 | 8/2013 | Abdou |
| 2013/0204306 A1 | 8/2013 | Walker et al. |

FOREIGN PATENT DOCUMENTS

| | | |
|---|---|---|
| EP | 1841376 A2 | 10/2007 |
| EP | 1847229 A2 | 10/2007 |
| FR | 2948553 A1 | 2/2011 |
| WO | WO2007037774 A1 | 4/2007 |
| WO | 2007056516 A2 | 5/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

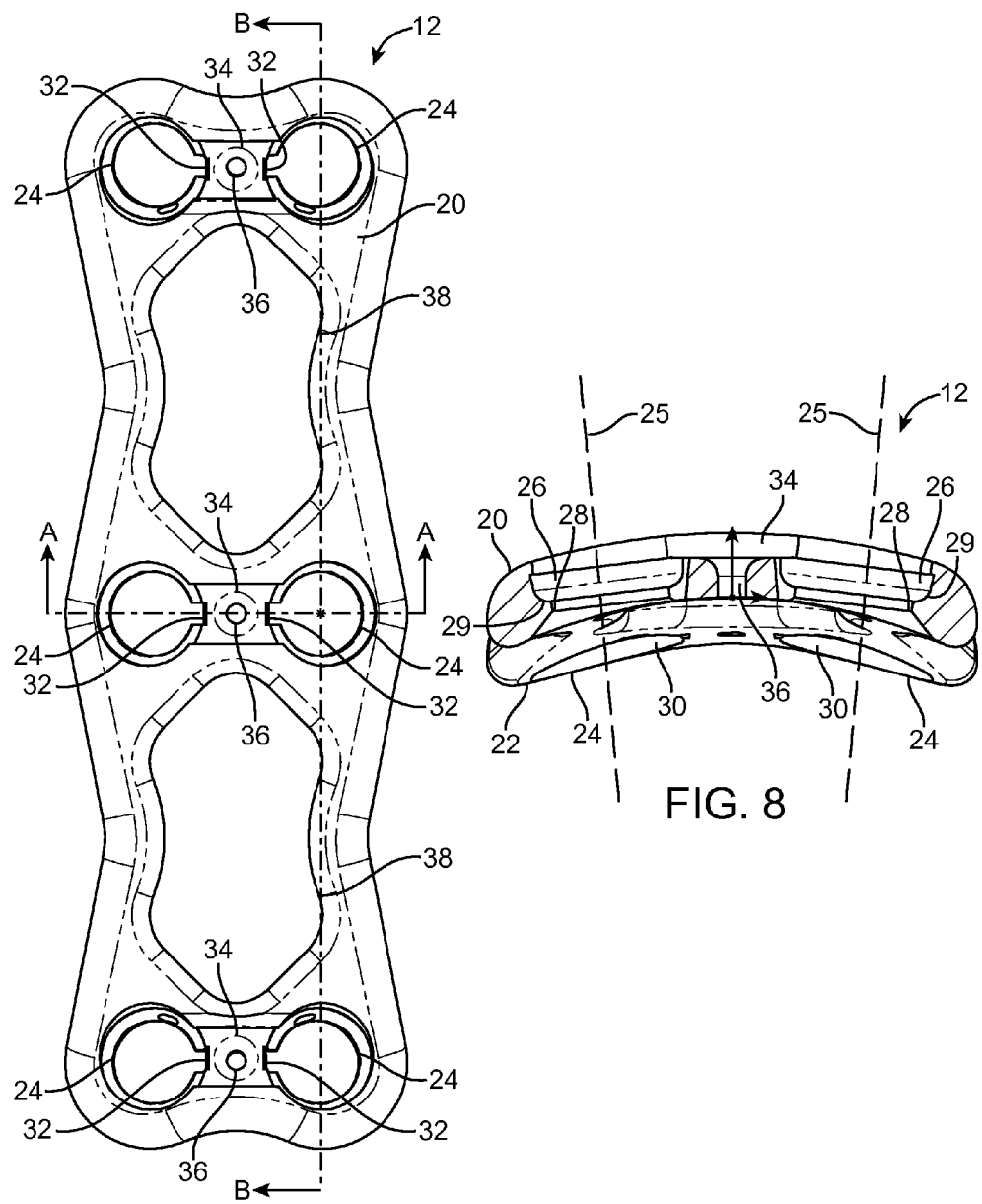

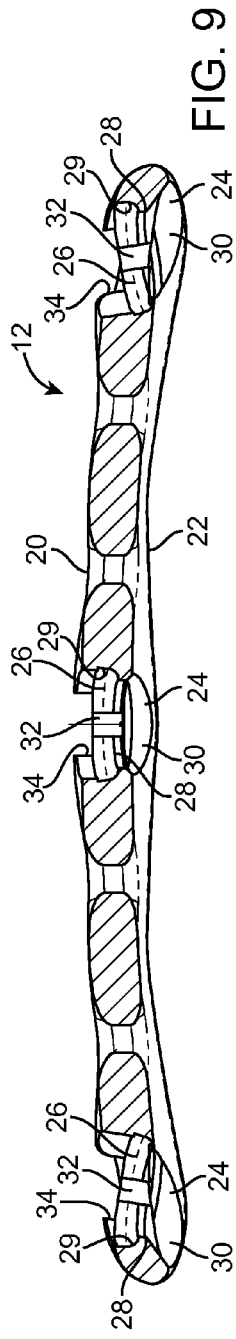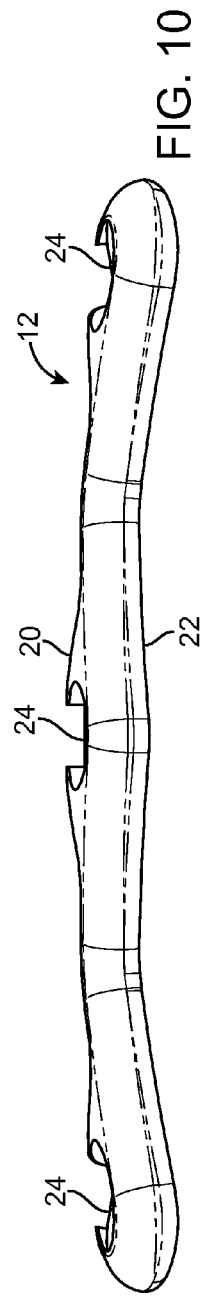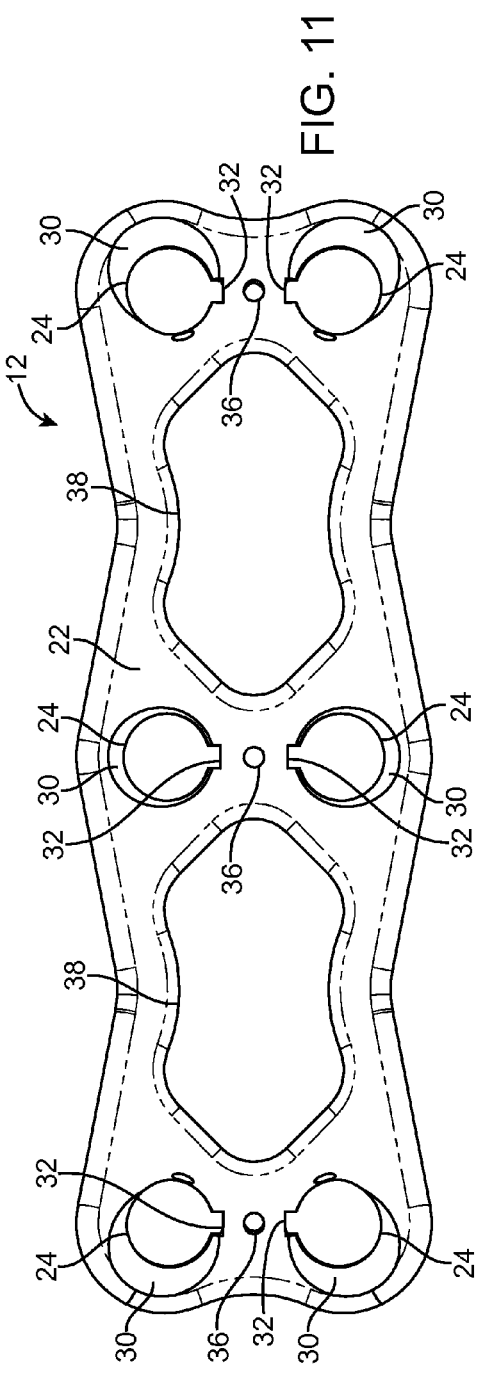

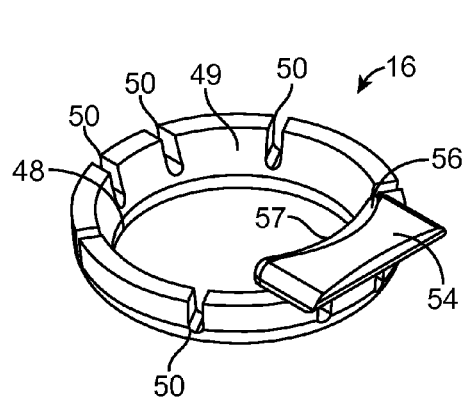 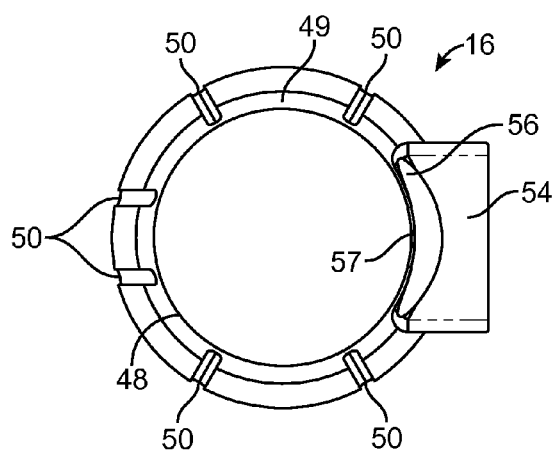
FIG. 15  FIG. 16
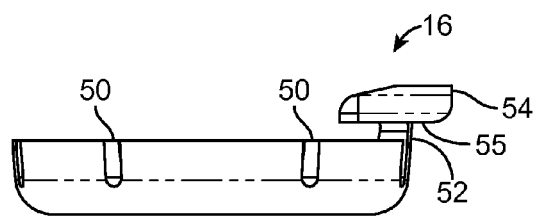
FIG. 17
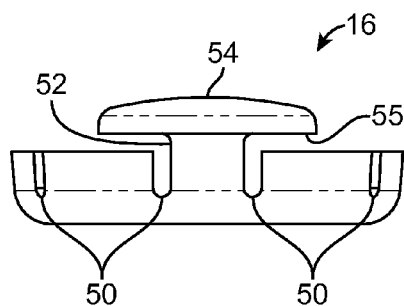 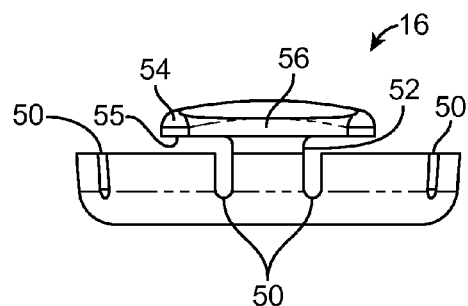
FIG. 18  FIG. 19

ANTERIOR CERVICAL PLATE

CROSS-REFERENCE TO RELATED APPLICATION

This application claims priority to and benefit of U.S. patent application Ser. No. 14/158,995 entitled "Anterior cervical plate" filed on Jan. 20, 2014 which is a continuation of U.S. patent application Ser. No. 13/185,641, filed on Jul. 19, 2011 now U.S. Pat. No. 8,668,723, issued on Mar. 11, 2014 entitled "Anterior cervical plate" all of which are incorporated herein by reference in its entireties.

FIELD

This invention relates to bone fixation plates and, more particularly, to fixation plates for the cervical spine that resist the back out of associated bone fasteners.

BACKGROUND

Anterior cervical plates are used for a variety of conditions to immobilize, stabilize or align cervical vertebrae. For example, after cervical spinal fusion surgery, cervical plates are used to add strength and rigidity to the adjoined vertebrae. Also, cervical plates secure vertebrae together where an intervening vertebra has been removed or replaced. In other cases, cervical plates are used to correct instability in the cervical spine caused by trauma, tumors, advanced degenerative discs, infection or congenital or acquired deformities.

A typical cervical plate includes an elongated rectangular plate that spans the distance between two or more vertebrae. The plate is curved to match the natural curvature of the spine at the location to which it is attached and bone screws are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Thereby, the plate bridges two vertebral bodies. More vertebrae may be connected with a longer plate and a corresponding increased number of bone screw apertures and bone screws inserted therethrough at the intervening vertebral levels.

The cervical spine can be surgically approached anteriorly or posteriorly. In anterior cervical fusion surgery, an incision is made and the spine is approached from the front of the patient. The carotid sheath, muscles, trachea and esophagus are moved laterally to expose the cervical spine. Holes are drilled into the vertebral bodies or self-tapping screws are employed. The cervical plate is properly aligned on the vertebrae for the receipt of mounting screws and the plate is carefully and firmly attached. Sometimes fusion is accompanied by a discectomy in which a herniated disc is removed and a graft device is placed between the vertebral bodies to assist in fusion across levels. The plate may also include a window formed generally at a location between the two pairs of screw apertures through which bone growth progress may be observed. With the plate in position, the vertebrae are held by the plate in desired spatial relationships and orientations relative to each other, pressure is removed from the nerve roots and pain caused by the herniated disc or other condition is relieved.

Over time, the interface between the screws and the bone may present some problems of stability. Due to the anatomical structure of the cervical spine and the extreme anatomical forces that are brought to bear on the skeleton and transmitted to the cervical spine, the screws securing the plate to the spine may vibrate or toggle out of position. Also, the degeneration of vertebral bone quality may result in the screws loosening or becoming dislodged. As a result, bone screws securing the plate to the spine may move or back out of the vertebral body and plate. Due to the relative location to the esophagus and other connective tissue, if the bone screw securing the plate to the cervical spine backs out, the bone screw could impinge on the adjacent tissue and increase pain. Also, loosened screws may result instability of the joint and lead to increased pain for the patient.

Therefore, there is a need to provide a new and improved anterior cervical plate that resists fasteners, such as bone screws, from backing out of the plate and also from being loosened with respect to the plate before migrating out. Not only an improved and effective fastener retaining mechanism is required, but also, its design cannot add undue bulk to the plate. The anterior cervical plate must have a low profile due to the proximity of the implant site to the esophagus and other sensitive surrounding tissue. It is also preferable to keep the plate as narrow as possible to reduce the chances that the lateral edges rise off from the underlying vertebral body and cause pain where the curvature of the plate does not exactly match the patient's anatomy. Furthermore, there is a need for the anterior cervical plate to withstand anatomical forces and be easily implanted. Also, the screw retaining mechanism must be easily activated by the surgeon. This invention, as described in the detailed description, sets forth an improved anterior cervical plate with anti-back out protection that meets these needs.

SUMMARY

According to one aspect of the invention, a bone plate is provided. The bone plate includes at least one through hole configured to receive a bone screw for attaching the plate to bone. The bone plate includes a retention ring disposed inside the at least one through hole. The retention ring includes a central aperture having a entry opening at a top surface. The retention ring includes a resiliently deflectable retention flange upwardly spaced from the top surface of the retention ring. The retention flange has a portion extending radially inwardly above the entry opening when in a normal undeflected position. The plate includes a bone screw having a head portion connected to a shank portion. The bone screw is configured for insertion into the through hole and into the central aperture of the retention ring such that at least a portion of the head portion is positioned distally of the retention flange. The plate includes a locking pin being movably connected with respect to the plate and mechanically coupled to at least one adjacent retention flange. The locking pin has at least one blocking surface. The bone plate includes a locked position in which the blocking surface of the locking pin is moved into a position adjacent to the retention flange to prevent outward deflection of the retention flange and thereby maintain the retention flange in the pathway of the entry opening and above the bone screw to prevent the bone screw from backing out of the through hole.

According to another aspect of the invention, a bone plate is provided. The bone plate includes a plate having at least one through hole configured to receive a bone screw for attaching the plate to bone. A retention ring is disposed inside the through hole. The retention ring includes a central aperture having a entry opening at a top surface and an exit opening at a bottom surface. The central aperture defines a central axis. The retention ring further includes an inner surface interconnected to an outer surface with each extending between the top surface and the bottom surface. The retention ring further includes a plurality of slots spaced circumferentially around the retention ring. The slots extend from the top surface towards the bottom surface to form deflectable tabs between the slots. The bone plate includes a bone screw having a head portion connected to a shank portion. The bone screw is configured for insertion into the through hole and into the central aperture of the retention ring. When the retention ring is inserted into the at least one through hole, the retention ring is configured such that the tabs are deflected inwardly towards the central axis such that the tabs cover at least a portion of the head portion of the bone screw that is inserted into the central aperture of the retention ring.

According to another aspect of the invention, a bone plate is provided. The plate has at least one through hole configured to receive a bone screw for attaching the plate to bone. A retention ring is disposed inside the through hole. The retention ring includes a central aperture having an entry opening at a top surface and an exit opening at a bottom surface. The central aperture defines a central axis. The retention ring further includes an inner surface and an outer surface extending between the top surface and the bottom surface. The retention ring also includes a resiliently deflectable retention flange upwardly spaced from the top surface of the retention ring. The retention flange has a portion that extends radially inwardly above the entry opening when in a normal undeflected position. The bone plate includes a bone screw having a head portion connected to a shank portion. The bone screw is configured for insertion into the through hole and into the central aperture of the retention ring such that at least a portion of the head portion is positioned distally of the retention flange. The bone plate also includes a locking pin connected to the plate and mechanically coupled to at least one adjacent retention flange. The locking pin has at least one blocking surface and at least one camming surface. The locking pin is movable to selectively position the blocking surface and camming surface adjacent to the retention flange. When positioned adjacent to the retention flange, the blocking surface is configured to prevent outward deflection of the retention flange to prevent the bone screw from backing out of the through hole. When positioned adjacent to the retention flange, the camming surface is configured to allow clearance for the retention flange to deflect outwardly to permit the bone screw to pass into and out of the retention ring.

According to another aspect of the invention, a method of using a spinal plate system is provided. The method includes the step of attaching a plate to bone wherein the plate comprises a plurality of through holes and a retention ring disposed in at least one through hole. The retention ring has a central aperture and a resiliently deflectable retention flange extending toward a central axis of the retention ring. The plate further includes at least one locking pin located adjacent to the at least one through hole and mechanically coupled to an associated adjacent retention flange. The method further including the steps of inserting a bone screw having a head connected to a threaded shank into each central aperture and through hole and inserting the bone screw into vertebral bone. Insertion of the bone screw is terminated when at least a portion of the head of the bone screw is located distally of the retention flange and the retention flange covers at least a portion of the bone screw or until a click is heard or felt. The method further includes the steps of rotating the at least one locking pin and terminating rotation of the at least one locking pin when the retention flange is locked in position or until a click is heard or felt.

BRIEF DESCRIPTION OF THE DRAWINGS

FIG. 7 is a top planar view of a plate according to the present invention.

FIG. 8 is a cross-sectional view taken along line A-A of FIG. 7 of a plate according to the present invention.

FIG. 9 is a cross-sectional view taken along line B-B of FIG. 7 of a plate according to the present invention.

FIG. 10 is a side elevation view of a plate according to the present invention.

FIG. 11 is a bottom planar view of a plate according to the present invention.

FIG. 15 is a top perspective view of a retention ring according to the present invention.

FIG. 16 is a top planar view of a retention ring according to the present invention.

FIG. 17 is a side elevation view of a retention ring according to the present invention.

FIG. 18 is a back end elevation view of a retention ring according to the present invention.

FIG. 19 is a front end elevation view of a retention ring according to the present invention.

DETAILED DESCRIPTION

Figure 1:
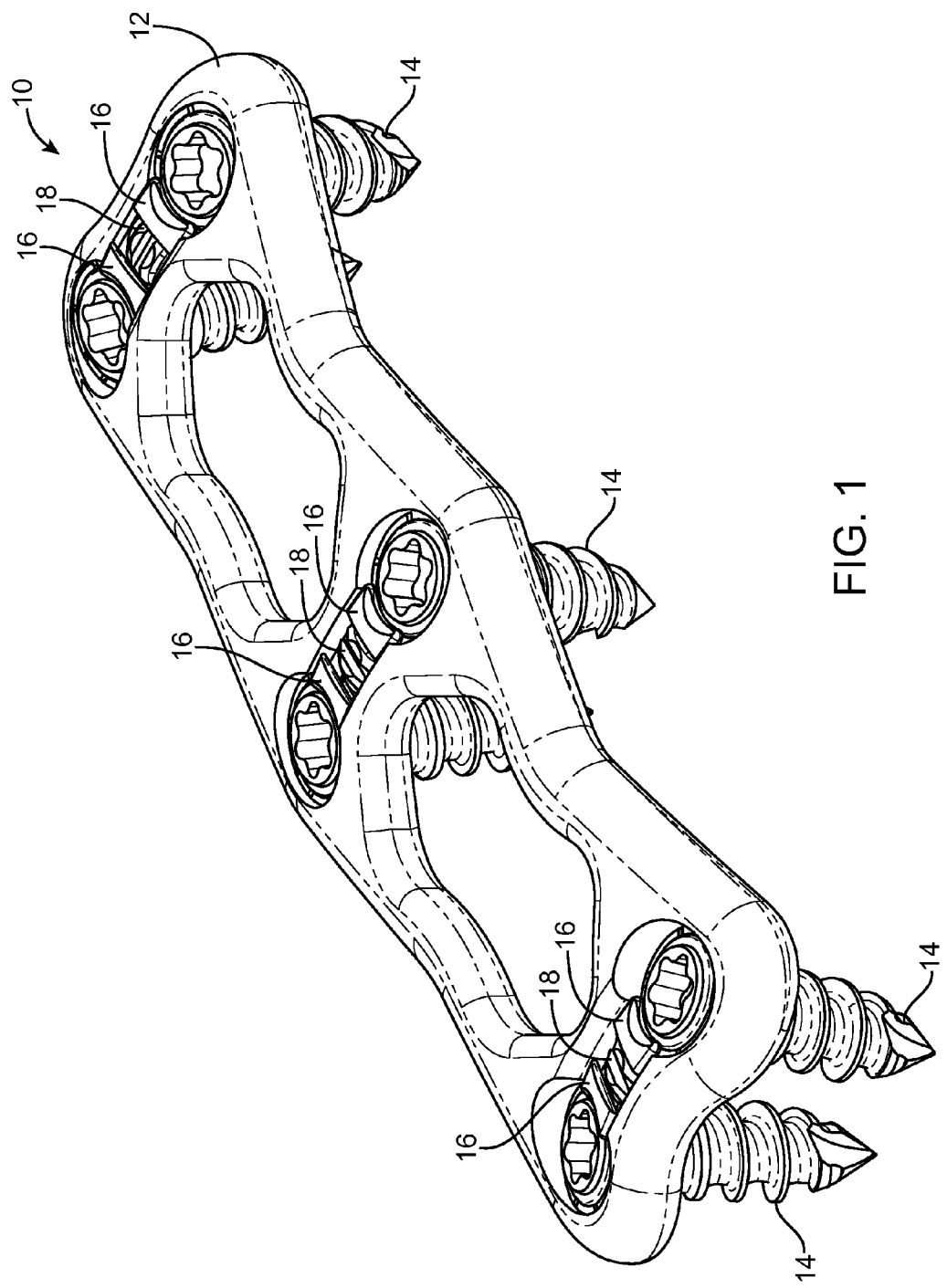
FIG. 1 is a top perspective view of an anterior cervical plate system according to the present invention.
Figure 2:
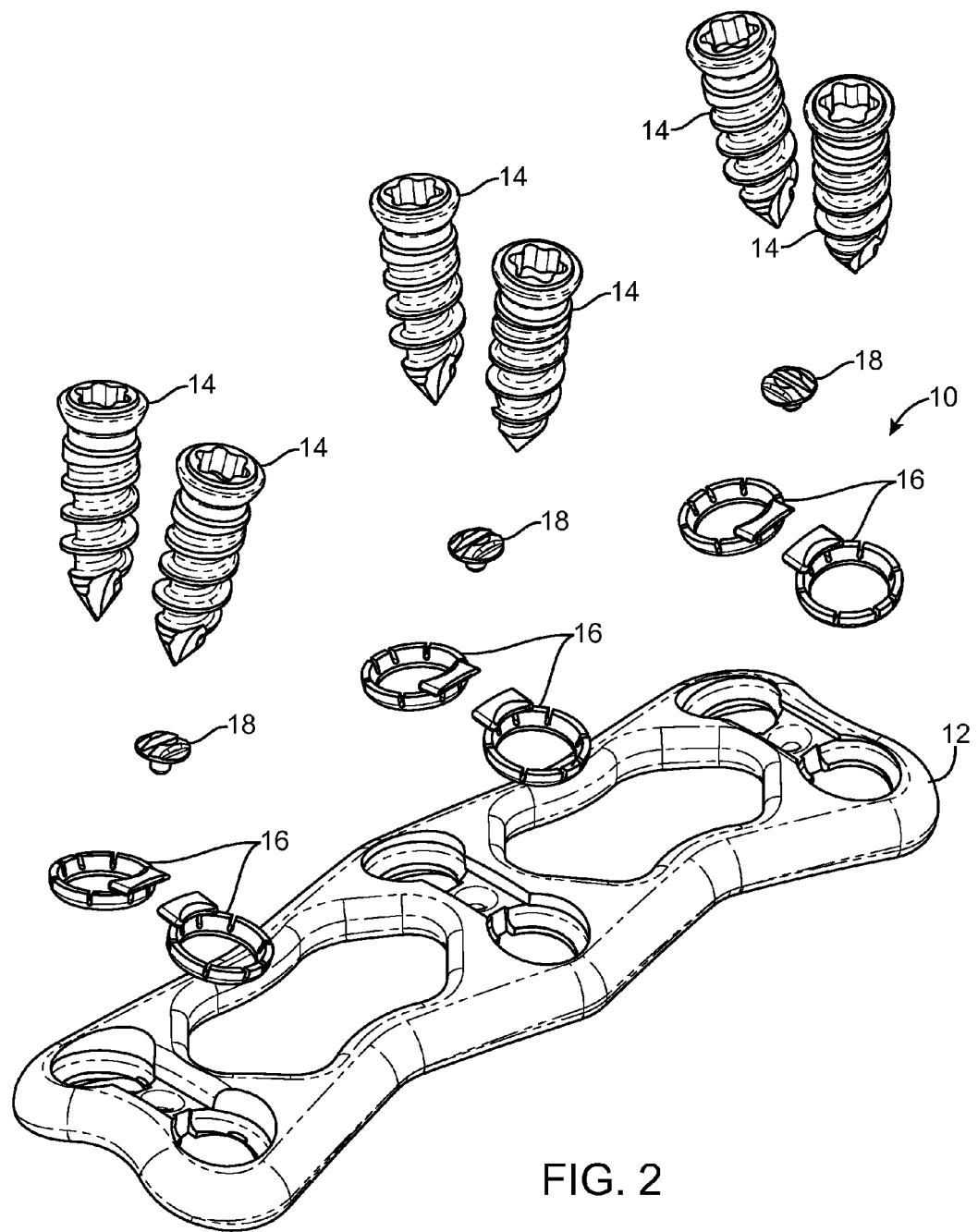
FIG. 2 is a top perspective exploded view of an anterior cervical plate system according to the present invention.
Figure 3:
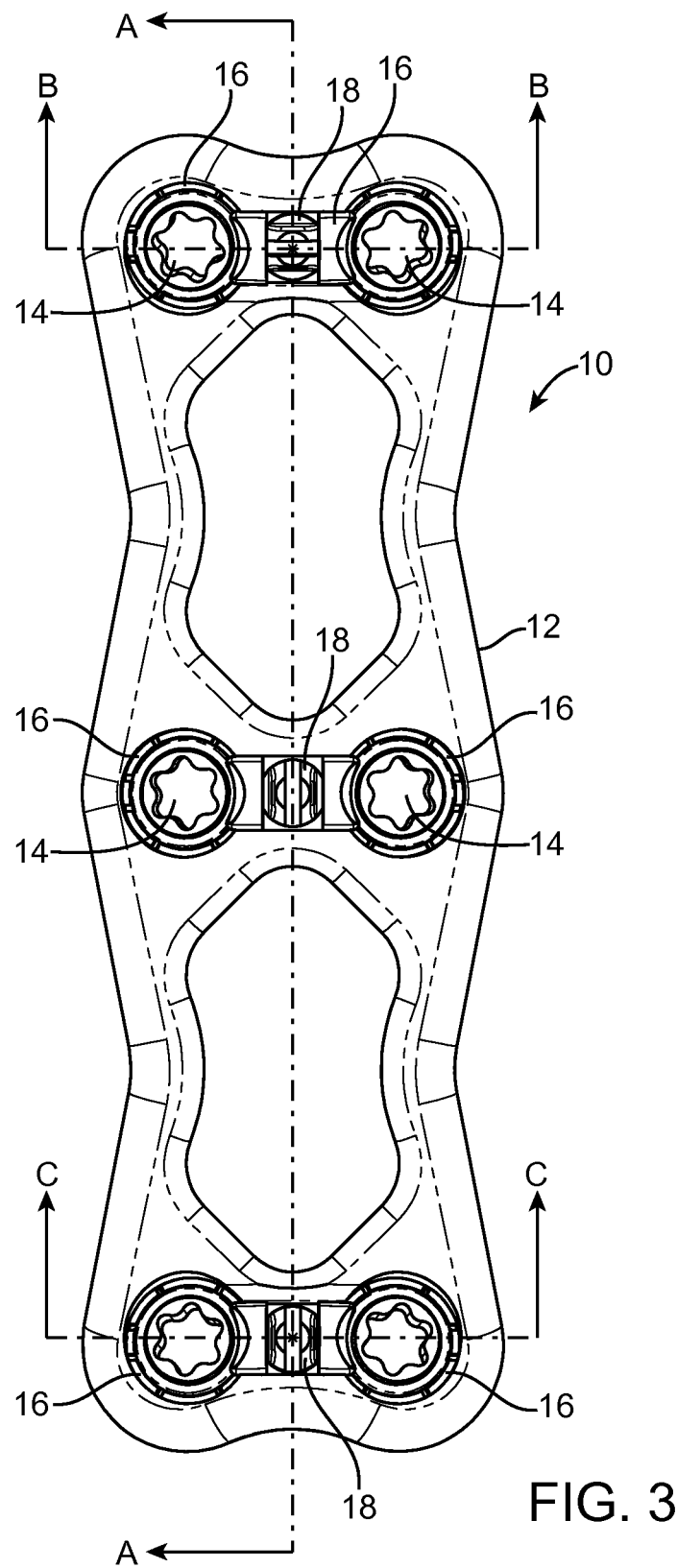
FIG. 3 is a top planar view of an anterior cervical plate system according to the present invention.
Figure 4:
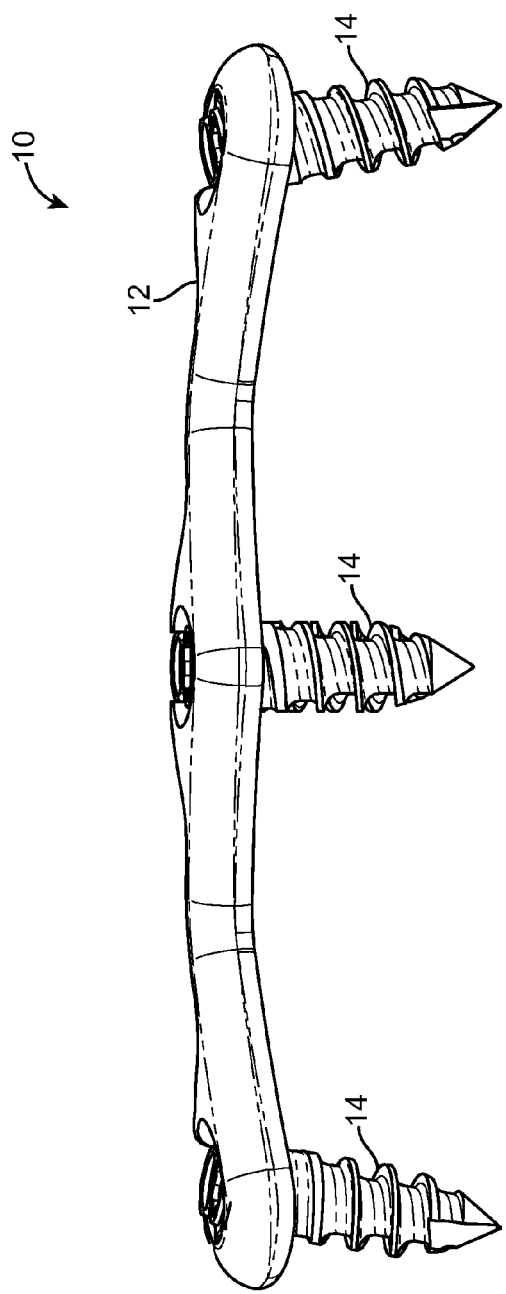
FIG. 4 is a side elevation view of an anterior cervical plate system according to the present invention.

FIGS. 1-5 depict a cervical plate system 10 according to one variation of the invention that may be used to stabilize or fuse vertebral bodies in the cervical or other region of the spine. The anterior cervical plate system 10 that is shown in FIGS. 1-5 is a two-level bone fixation plate that is configured to span across and fixate three vertebrae of the cervical spine although the cervical plate system 10 may be a single level or any multilevel anterior cervical plate spanning two or more vertebral bodies. The anterior cervical plate system 10 comprises a plate 12 having fasteners 14 passed through retention rings 16 locked into place with locking pins 18.

Turning now to FIGS. 6-11, the plate 12 will now be described in greater detail. The plate 12 includes an upper surface 20 or anterior surface that faces the patient's soft tissue and esophagus when installed and a lower surface 22 or posterior surface facing the vertebral bodies to be immobilized. The upper surface 20 and lower surface 22 are interconnected by curved side walls and end walls to form a generally rectangular shape that is symmetrical about a midline. As best seen in FIGS. 8 and 9, the gently curved structure of the rectangular plate 12 complements the natural curved structure of the vertebral bodies and lordotic curvature of the cervical spine. The corners of the plate are rounded to reduce or eliminate irritation of the esophagus and the surrounding tissue. The plate 12 is sized and shaped for use on an anterior aspect of the cervical spine although one skilled in the art may use the device in other regions of the spine and other skeletal fixations. The plate 12, which resides atop the vertebral bodies, has a low profile as seen in FIG. 10 so as to minimally impinge on adjacent tissues.

The plate 12 and other components of the cervical plate system 10 are made from suitable biocompatible material such as stainless steel, titanium and or any other metal or metal alloy. One or more components may be made of nonmetal materials including but not limited to polymer, carbon reinforced polyetheretherketone (PEEK) or one or more biocompatible ceramics. The plate 12 may be additionally configured to promote bone ingrowth to the plate such as a portion of the plate being made of porous material or being roughened by mechanical blasting or plasma spraying with metal particles of one or more sizes. The plate 12 may also be coated with bio-active material, therapeutic agents for enhancing bone fusion and ingrowth, bone morphogenic proteins, growth factors and the like.

Still referencing FIGS. 6-11, the plate 12 includes a plurality of through holes 24 extending through the cervical plate 12 from the upper surface 20 and through the lower surface 22. The holes 24 are configured to receive bone fasteners 14 passed there through. Each hole 24 includes a head-receiving portion 26 near the upper surface 20 connected to a smaller shank-receiving portion 28 near the lower surface 22 to, thereby, in one variation, provide a seat for the head portion of the fastener 14 at a ledge 29 formed at the intersection of the head-receiving portion 26 and shank-receiving portion 28. The head-receiving portion 26 is recessed from the top surface 20 as best seen in FIGS. 8 and 9 such that the head of the fastener 14 does not protrude beyond the upper surface 20 of the plate 12 in order to maintain a low profile for the plate 12. Each through hole 24 has a larger exit opening 30 at the lower surface 22 to allow room for the angulation of inserted fasteners 14. In one variation, the head-receiving portion 26 also provides a receiving well for the retention ring 16. Accordingly, the head-receiving portion 26 is shaped to complement the shape of the retention ring 16. For example, the head-receiving portion 26 forms a part-spherical seat or curved surface configured for a complimentary part-spherical or curved outer surface of the retention ring 16. In one variation, the size of the through hole 24 is configured such that the head-receiving portion 26 and shank-receiving portion 28 are both large enough to allow a bone fastener 14 to pass all the way through the plate without the presence of a retention ring 16 and wherein the presence of the retention ring 16 in the through hole 24 reduces the size of the through hole 24 such that the head portion of the fastener 14 is not allowed to pass through the retention ring 16. In another variation, the shank-receiving portion 28 of the through hole 24 is smaller than the head-receiving portion 26 without the presence of a retention ring 16 such that the head portion of a fastener 14 is not allowed to pass into the shank-receiving portion 28 of the through hole 24 and wherein the presence of the retention ring 16 further reduces the opening at the head-receiving portion 26 of the through hole 24. A notch 32 is formed in at least one of the head-receiving portion 26 and shank-receiving portion 28. The notch 32 prevents the retaining ring 16 from rotating or moving out of place with respect to the plate 12. In one variation, the notch 32 creates space within which the neck and flange of the retention ring 16 may move and flex as will be discussed in greater detail below. An undercut (not shown) in the through hole 24 such as in the location of the head-receiving portion 26 may be formed and configured to mate with the retention ring 16 to, thereby, couple the retention ring 16 to the through hole 24 as the retention ring 16 is compressed and then inserted into or under the undercut. In another variation, the through hole 24 is slightly elliptical in shape that matches a slightly elliptical retention ring 16 which can be inserted in the conforming direction and then rotated into a non-conforming orientation to be retained within the through hole 24 by compression fit engagement therewith.

Figure 5:
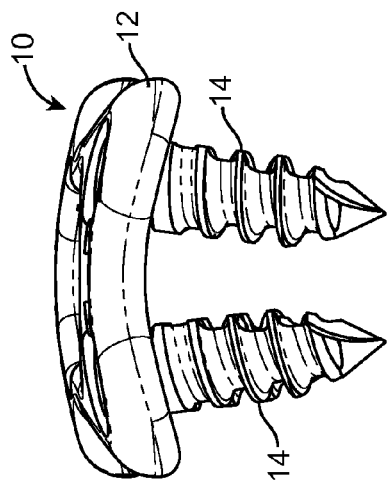
FIG. 5 is an end elevation view of an anterior cervical plate system according to the present invention.
Figure 6:
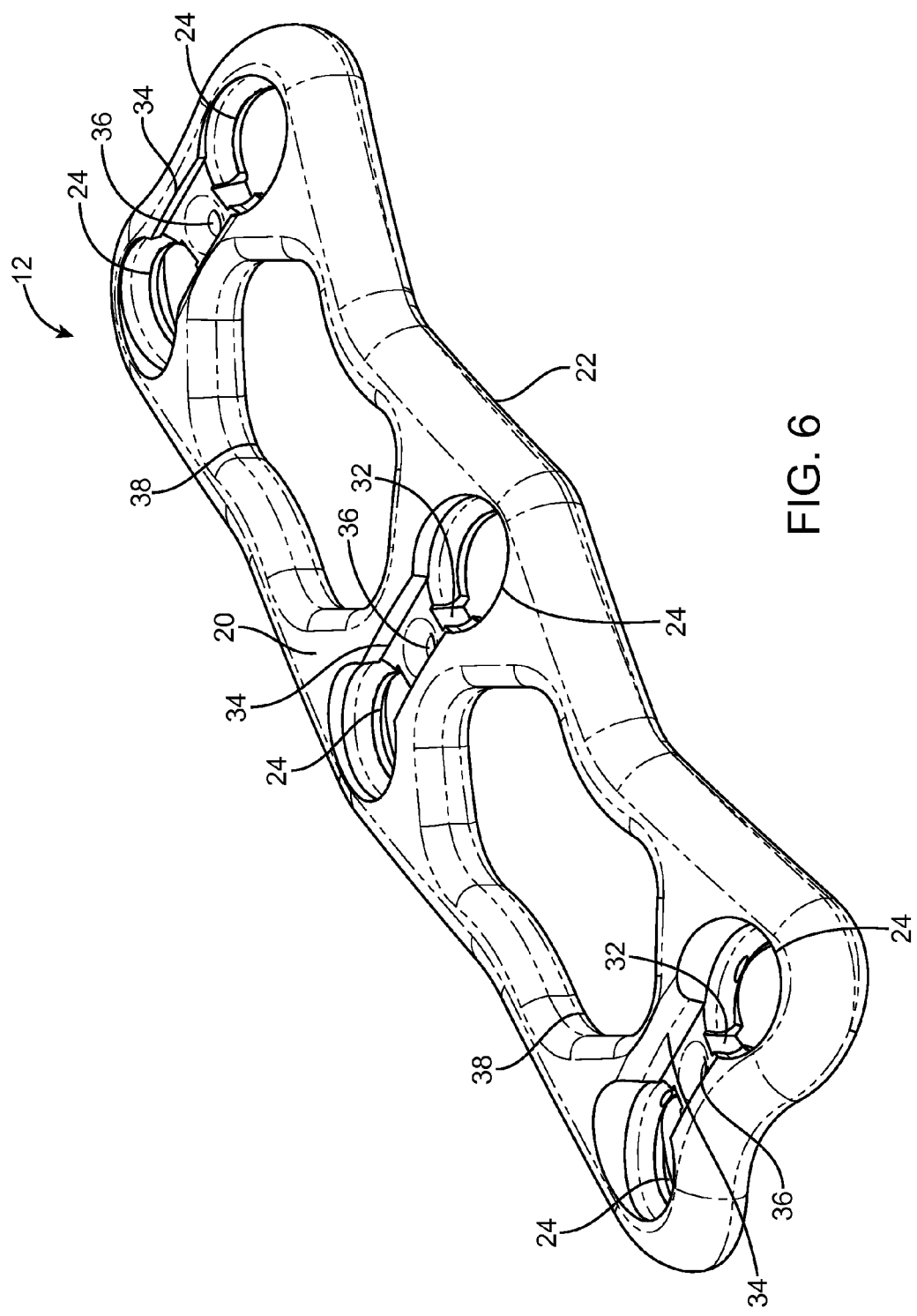
FIG. 6 is a top perspective view of a plate according to the present invention.

FIGS. 6-12 depict a plate 12 having three sets or three pairs of fastener through holes 24 spaced-apart along the plate centerline for driving fasteners 14 into and stabilizing three vertebral bodies for creating a two-level construct. Each set of fastener through holes 24 includes two holes 24 spaced apart from each other along the centerline of the anterior cervical plate 12. Each set or pair of through holes 24 is adapted for receiving two fasteners 14 to be driven into a single vertebral body. As best seen in FIG. 8, the longitudinal axes 25 of a pair of through holes 24 diverge relative to each other such that a pair of fasteners 14 placed therein diverge slightly relative to each other at a desired angled as best seen in FIG. 5.

The plate 12 further includes a recess 34 located between the through holes 24 of each pair of through holes 24. The recess 34 is configured for receiving a locking pin 18 such that the locking pin 18 does not protrude from the upper surface 20 of the plate 12 in order to maintain the desired low profile. A locking pin aperture 36 is formed in the recess 34 at the centerline for coupling the locking pin 18 to the plate 12. The plate 12 also includes two larger openings 38 located between each pair of through holes 24 that effectively reduce the overall weight of the plate 12 and provide a visualization pathway to monitor bone graft progress between the vertebral bodies.

Figures 12, 13:
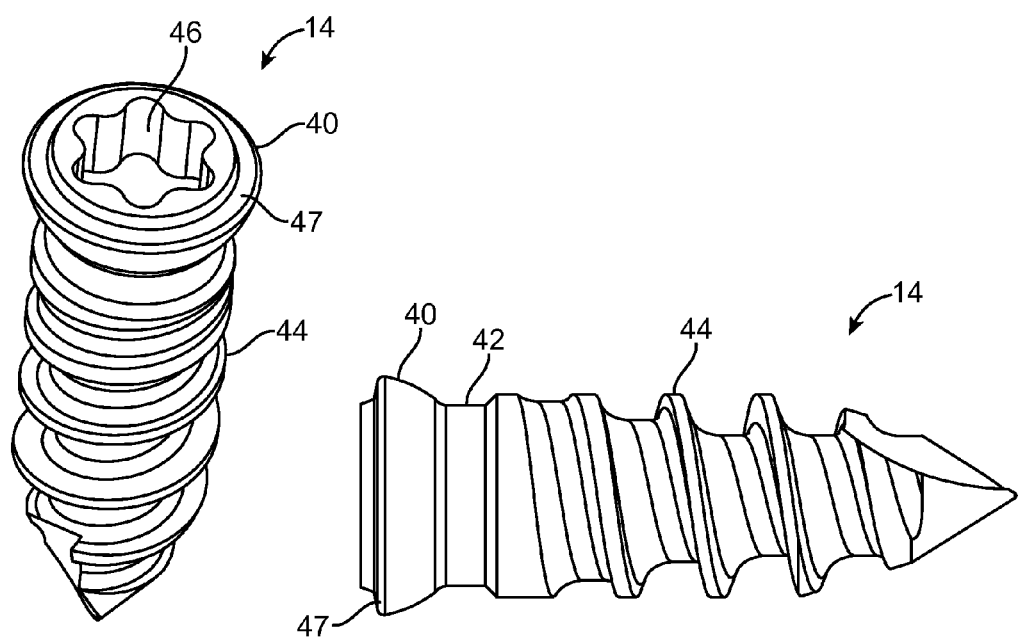
FIG. 12 is a top perspective view of a bone fastener according to the present invention.
FIG. 13 is a side elevation view of a bone fastener according to the present invention.
Figure 14:
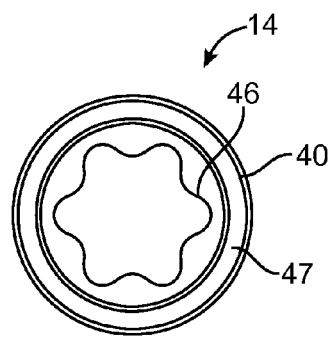
FIG. 14 is a top planar view of a bone fastener according to the present invention.
Figure 20:
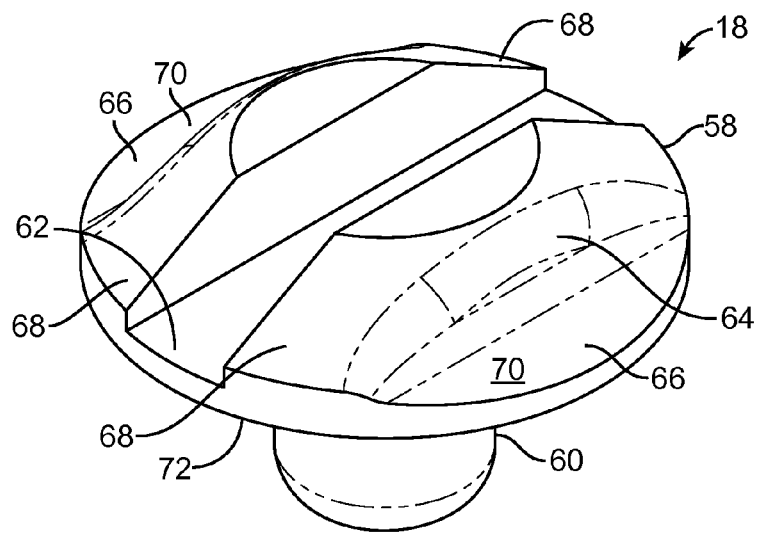
FIG. 20 is a top perspective view of a locking pin according to the present invention.
Figure 21:
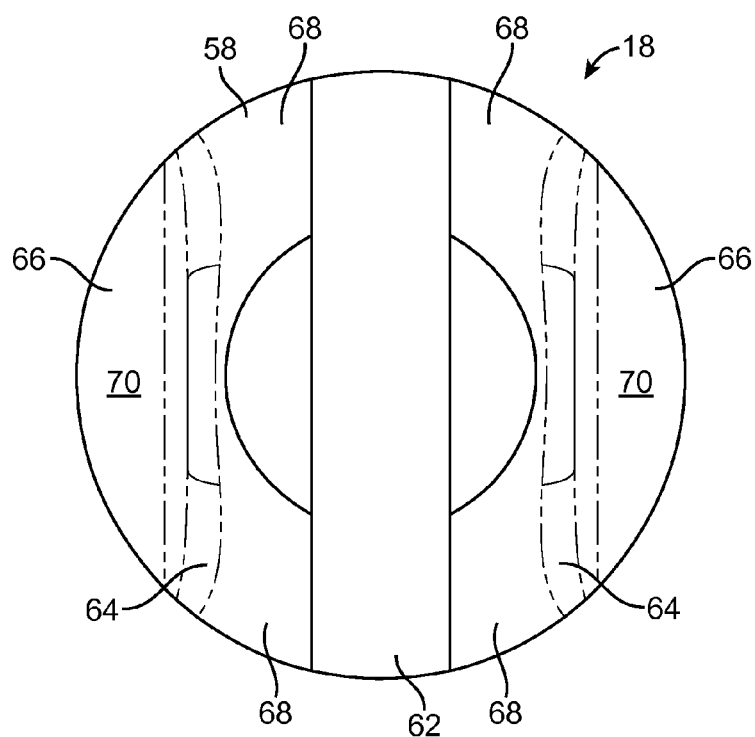
FIG. 21 is a top planar view of a locking pin according to the present invention.
Figure 22:
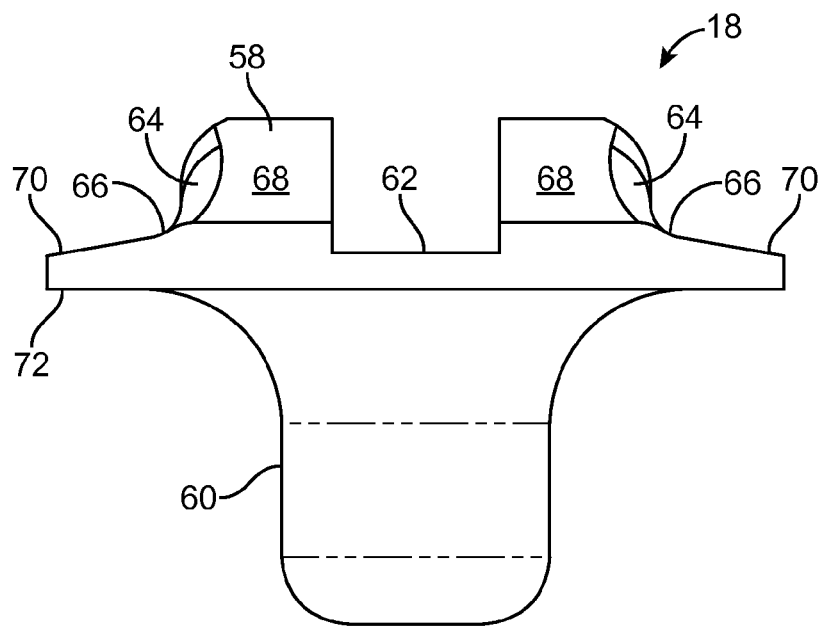
FIG. 22 is a side elevation view of a locking pin according to the present invention.

With particular reference to FIGS. 12-14, an exemplary orthopedic fastener 14 that is preferably used with the cervical plate system 10 of the present invention is a bone screw 14. The bone screw 14 includes a screw head 40, neck 42 and threaded shank 44. The head 40 includes a ledge 47 which is a flat surface along at least a portion of the perimeter of screw head 40. The head 40 includes an instrument recess 46 for receiving a complementary tip of a surgical tool. A substantially hexagonal, daisy-shaped recess 46 is shown in FIGS. 12-14, however, the recess 46 can be of any shape that allows a surgical tool to drive the bone screws 14 into the vertebral column. The head 40 of the bone screw 14 corresponds to the shape of the inside of the associated retention ring 16 or, in an alternative variation, to the shape of the head-receiving portion 26 of the through hole 24. Various bone screws 14 may be employed including ones capable of polyaxial, variable angle or fixed angled orientation with respect to the plate 12 with or without the ability to be locked down at a desired angle or orientation with respect to the plate 12. The bone screws 14 are preferably self-tapping, however, other screws requiring holes to be drilled or pre-tapped can also be employed.

Turning now to FIGS. 15-19, the retention ring 16 will now be discussed. The retention ring 16 has a circular or slightly elliptical profile and a central aperture 48 having a central axis and defining an entry opening at a top surface of the retention ring 16 and an exit opening at the bottom surface of the retention ring 16. The retention ring 16 is configured for insertion into and being received inside a through hole 24 of the plate 12. The central aperture 48 has a width greater than the width of the threaded shank 44 of a bone screw 14 where the width is the major diameter of the threads or, in an alternative variation, greater than the width of the minor diameter of the threads. However, the width of the central aperture 48 is not larger than the width of the head of a fastener 14 such that the head 40 of the fastener is not allowed to completely pass through the central aperture 48. The head 40 is received at the inner surface 49 of the retention ring 16, which is sized to prevent lateral movement of the fastener 14 and shaped to complement the shape of the screw head 40. For example, the inner surface 49 of the retention ring 16 forms a part-spherical or curved seat configured for multi-angular articulation with a complimentary part-spherical or curved surface of the screw head 40 of fastener 14. Of course, the complementary surfaces of the retention ring 16 and screw head 40 are not limited to being part-spherical or curved but may be of any shape. The inner surface 49 of the retention ring 16 generally slopes upwardly from the bottom surface to the top surface of the retention ring 16.

A plurality of slots 50 are formed in the ring 16. The slots 50 extend approximately halfway from the top surface of the ring 16 toward the bottom surface of the ring 16. The slots 50 form a plurality of circumferential tabs at the upper surface around the central aperture 49. These slots 50 weaken the upper portion of the ring 16 such that the retention ring 16 is slightly compressible. The compressibility of the ring 16 affords advantages for increasing the purchase of the screw head 40 to the plate 12 in addition to allowing the retention ring 16 to be inserted and retained in the plate 12. The retention ring 16 is easily inserted into the head-receiving portion 26 which serves as a well for the retention ring 16. In one variation, the retention ring 16 may include an externally protruding annular retention lip (not shown) that would snap into an undercut or the like formed in the plate 12 and configured for connecting the retention ring 16 to the plate 12. In another variation, the tabs are deflected slightly inwardly towards the central axis upon insertion into a through hole 24 wherein the inwardly deflected tabs advantageously create an undercut for retaining the screw head 40 firmly inside the plate 12 through hole 24. The slightly inwardly deflected tabs serve as fingers grasping and contacting slightly over and around at least a portion of the screw head 40.

Still referencing FIGS. 15-19, extending upwardly from the top surface of the ring 16 is a retention flange 54 connected to a neck 52. The retention flange 54 includes a portion that projects inwardly towards the center of the ring 16 and is selectively imposed into the pathway of a fastener 14. In particular, the retention flange 54 extends into the projection of the entry opening of the central aperture 48 such that a fastener 14 moving into and through the central aperture 48 would encounter resistance from the retention flange 54. The retention flange 54 includes a scalloped portion 56 that serves as a ramp for guiding a bone fastener 14 and for receiving a lateral force component exerted by the fastener 14 onto the retention flange 54 as a bone fastener 14 passes into the central aperture 48 and into the through hole 24. As a result of the lateral force component exerted upon the retention flange 54 by an entering fastener 14, the neck 52 is adapted to flex causing the retention flange 54 to deflect slightly outwardly to allow a bone fastener 14 to continue to pass through the central aperture 48. After the fastener 14 passes beyond the retention flange 54, the retention flange 54 is configured to snap back to its normal un-flexed or partially flexed position such that at least a portion of the retention flange 54 projects back inwardly toward the center of the ring 16 and into the pathway of the fastener 14 thereby, forming a stop that prevents the fastener 14 from backing out. The undersurface 55 of the retention flange 54 overlays the head 40 of the fastener 14 either touching the head 40 of the fastener 14 or laying spaced apart from the head 40 of the fastener 14 and, thereby, preventing the fastener 14 from backing out. The snapping back of the retention flange 54 as a screw ledge 47 passes beyond the retention flange 54 advantageously provides the surgeon with an audible and/or haptic signal or feedback that the screw 14 has been advanced far enough and the surgeon can stop driving or advancing the screw 14 into the vertebral bone. As a result, the audible or haptic click notifies the surgeon that the screw 14 is in position and prevents the surgeon from applying too much torque. As best seen in FIG. 16, the inner facing surface 57 of the retention flange 54 is curved to match the curvature of the fastener 14 and configured to cover a portion of the ledge 47 along the perimeter of the screw head 40. In another variation, the retention ring 16 is integrally formed with the plate 12 such that a neck 52 and retention flange 54 project from a surface of the plate 12.

Turning to FIGS. 20-23, the locking pin 18 will now be discussed. The locking pin 18 includes a main body 58 connected to a post 60. The post 60 extends from the bottom surface 72 of the main body 58 along the longitudinal axis of the locking pin 18. The post 60 is configured to be inserted into the locking pin aperture 36 of the plate 12 and connected to the plate 12 such that the locking pin 18 can rotate relative to the plate 12 about the longitudinal axis. The locking pin 18 may include an additional coupling element (not shown) for coupling the locking pin 18 to the cervical plate 12 in a manner that maintains the locking pin 18 rotatably coupled to the plate 12. Of course, the locking pin 18 is not limited to rotational movement with respect to the plate 12 and can be designed for linear movement with respect to the plate 12 for example. Whereas the post 60 is inserted into the plate 12, the main body 58 of the locking pin 18 resides above the upper surface 20 of the plate 12 in the location of the recess 34 next to a through hole 24 or in another variation as shown in the figures in the location of the recess 34 between two adjacent through holes 24 such that the main body 58 of the locking pin 18 does not extend beyond the outer profile of the plate 12 maintaining the smooth low profile of the plate 12. The locking pin 18 is shown in the figures to have a circular top profile, however, the invention is not so limited and the locking pin 18 may be any operable shape.

The locking pin 18 is means for locking or unlocking the retention flange 54 of the retention ring 16. The locking pin 18 includes a camming surface 66 and a blocking surface 68 formed in the main body 58. The locking pin 18 is positioned next to the retention ring 16 such that the camming surface 66 and blocking surface 68 in turn contact at least a portion of the neck 52 and/or at least a portion of the retention flange 54 of the stationary retention flange 54. The camming surface 66 is adjacent to the blocking surface 68 on the main body 58 and configured such that, with rotation of the locking pin 18, at least a portion of the neck 52 and/or at least a portion of the retention flange 54 that is in contact with a the camming surface 66 is led into or cammed into being in contact with the blocking surface 68 to lock the retention flange 54 in position. A stop (not shown) may be formed at the end of the blocking surface 68 to prevent further rotation of the locking pin 18 in the same direction. In one variation without a stop, continued rotation of the locking pin 18, at least a portion of the neck 52 and/or at least a portion of the retention flange 54 that is in contact with the blocking surface 66 remains intact with the blocking surface 66 throughout the rotation of the locking pin 18 until reaching and contacting the same camming surface 66. Such a variation of the locking pin 18 is employed adjacent to one retention ring 16 and is designed to lock one retention flange 54. Of course, rotation of the locking pin 18 in the opposite direction will lead or cam the at least a portion of the neck 52 and/or the at least a portion of the retention flange 54 that is in contact with a the blocking surface 68 into being in contact with the camming surface 66 to unlock the retention flange 54.

While still referencing FIGS. 20-23 and with particular reference to FIGS. 24-27, in the variation of the locking pin 18 that is shown in FIGS. 20-23, the locking pin 18 is located between two adjacent retention rings 16a, 16b and the locking pin 18 is configured with two oppositely disposed camming surfaces 66a, 66b and two oppositely disposed blocking surfaces 68a, 68b for locking or unlocking the retention flanges 54a, 54b of two adjacent retention rings 16a, 16b simultaneously. In such a variation, a first camming surface 66a is adjacent to a first blocking surface 68a and the second camming surface 66b is adjacent to the second blocking surface 68b and configured such that, with rotation of the locking pin 18, at least a portion of the neck 52 and/or at least a portion of a first retention flange 54a of a first retention ring 16a that is in contact with the first camming surface 66a is led or cammed into being in contact with the first blocking surface 68a and at least a portion of the neck 52 and/or at least a portion of a second retention flange 54b of a second retention ring 16b that is in contact with the second camming surface 66b is led or cammed into being in contact with the second blocking surface 68b to lock the retention flanges 54a, 54b of the first and second retention rings 16a, 16b simultaneously. Stops may be formed at the end of each blocking surface 68a, 68b to prevent further rotation in the same direction. Rotation of the locking pin 18 in the opposite direction will result in the retention flanges 54a, 54b that are in contact with the blocking surfaces 68a, 68b, respectively, being in contact with the camming surfaces 66a, 66b, respectively, to simultaneously unlock the retention flanges 54a, 54b, respectively. In one variation, the locking pin need only be rotated by 90 degrees to move from an unlocked position to a locked position or from a locked position to an unlocked position.

Turning back to FIGS. 20-23, the main body 58 further includes a slit 62 configured to receive an instrument, such as a screwdriver, to turn the locking pin 18 with respect to the plate 12. Although a slit 62 that is configured to match a flat screwdriver is shown in FIGS. 20-23, a recess having any shape that is complementary to the instrument employed to activate, move or rotate the locking pin 18 may be used.

Still referencing FIGS. 20-23 and further referencing FIGS. 24-27, the main body 58 includes two scallops 64a, 64b located on either side of the slit 62. A camming surface 66 is formed in the location of each scallop 64. In one variation, the locking pin 18 is configured to be disposed in the cervical plate 12 adjacent to a pair of through holes 24 and configured to simultaneously lock two adjacent retention rings 16 residing in the pair of adjacent through holes 24 as discussed above. In such a variation, the locking pin 18 includes a first camming surface 66a at the first scallop 64a and a second camming surface 66b at the second scallop 64b configured to simultaneously cam against two adjacent retention rings 16a, 16b.

Figure 23:
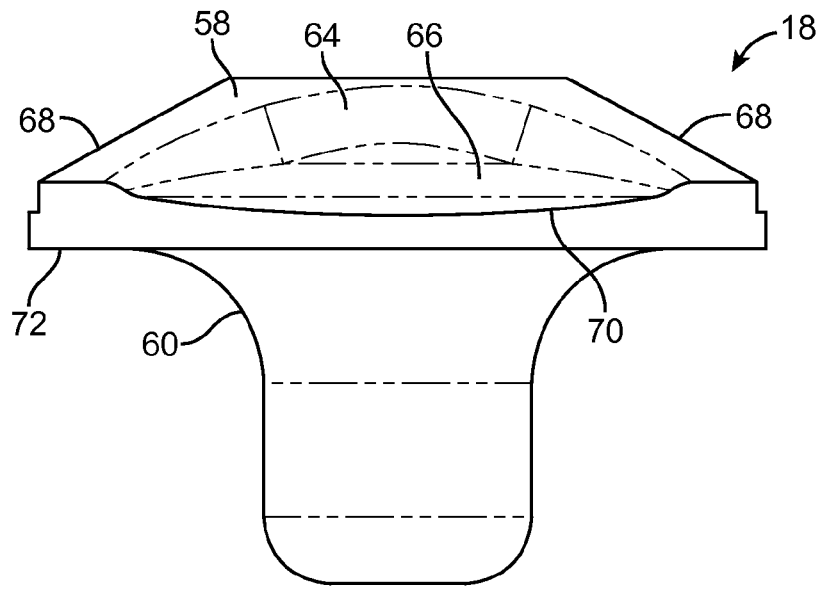
FIG. 23 is a side elevation view taken 90 degrees to FIG. 22 of a locking pin according to the present invention.
Figure 25:
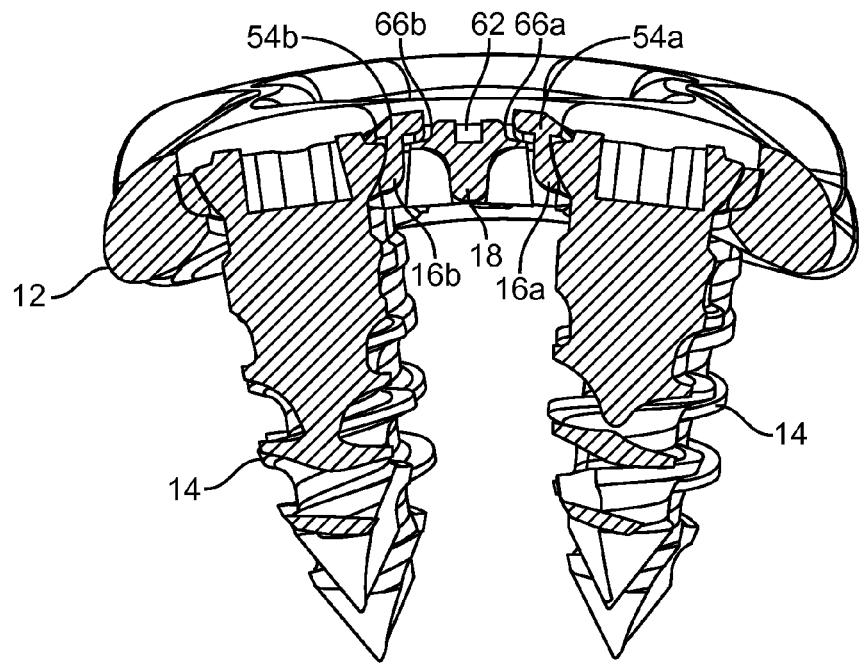
FIG. 25 is a cross-sectional view taken along line C-C of FIG. 3 of an anterior cervical plate system with the locking pin in an unlocked position according to the present invention.
Figure 27:
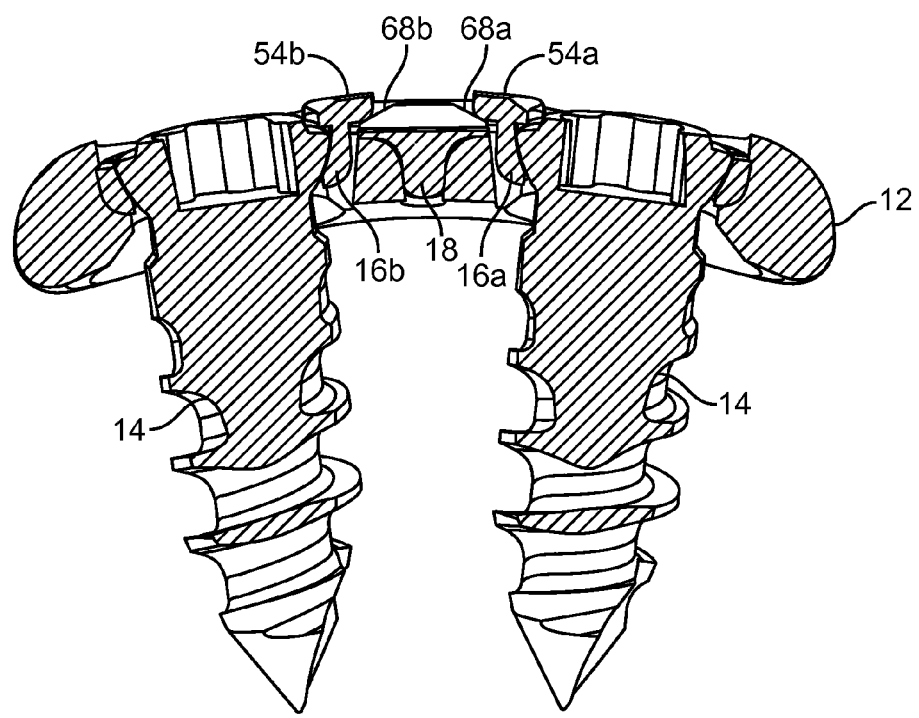
FIG. 27 is a cross-sectional view taken along line B-B of FIG. 3 of an anterior cervical plate system with the locking pin in a locked position according to the present invention.

Generally, the camming surface 66 comprises a gently curved, or angled, wedge-like surface having a thickness that varies along the top surface 70 of the wedge. The bottom of the wedge coincides with the bottom surface 72 of the main body 58 and is substantially planar. The camming surface 66a of a wedge at the first side varies along the outer perimeter and is the thinnest at a location 90 degrees to the slit 62 as best seen in FIG. 23. The wedge increases in thickness along the perimeter in a direction toward 0 degrees and 180 degrees as can be clearly seen in FIG. 22. The thickness of the camming surface 66a also increases toward the longitudinal axes of the locking pin 18. The camming surface 66b of a wedge at the second side is the thinnest at a location 270 degrees to the slit 62. The wedge increases in thickness in a direction towards 180 degrees and 360 degrees as can also be seen in FIG. 23. The thickness of the camming surface 66b also increases toward the longitudinal axes of the locking pin 18. The camming surface 66 is sized and configured such that, upon assembly of the plate system 10, at least a portion of the camming surface 66 is positioned underneath a portion of the retention flange 54 that extends outwardly beyond the perimeter of the retention ring 16 as best seen in FIGS. 25 and 27. In one variation, the camming surface 66 is angled or curved to cam underneath or against the retention flange 54 and/or neck 52. In the variation in which the locking pin 18 includes two camming surfaces 66a, 66b, at least a portion of each camming surface 66a, 66b is positioned underneath each retention flange 54a, 54b of the pair with each camming surface 66a, 66b being angled or curved to cam underneath or against the retention flanges 54a, 54b and/or necks 52a, 52b as best seen in FIGS. 25 and 27.

Figure 24:
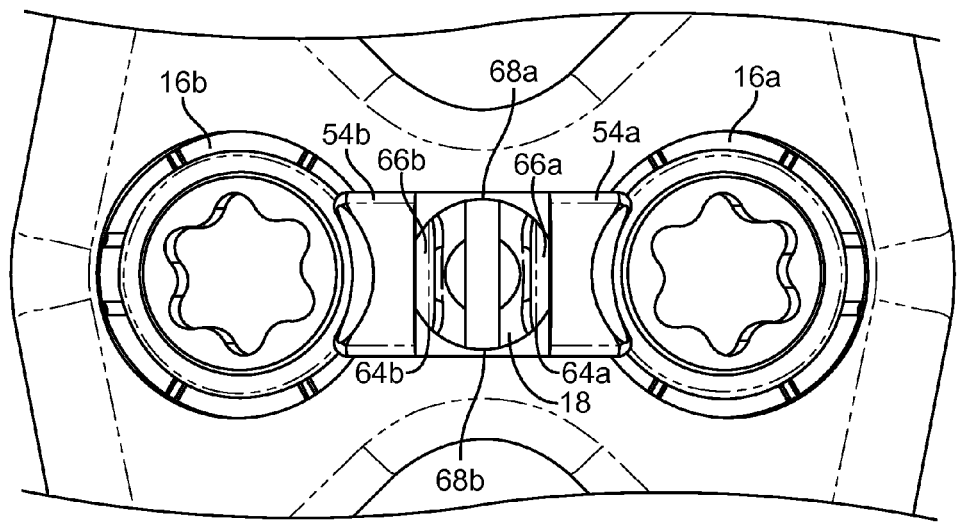
FIG. 24 is a top sectional view of an anterior cervical plate system with a locking pin in an unlocked position according to the present invention.

From a starting position at 90 degrees from the slit 62 at a location configured to contact the retention flange 54, the portion of the camming surface 66 that is in contact with the retention ring 16 is the thinnest and, with rotation of the locking pin 16 in a clockwise or counterclockwise direction, the portion of the camming surface 66 that is in contact with the retention ring 16 increases in thickness. In one variation, the camming surface 66 does not contact the retention ring at 90 degrees. In the variation in which the locking pin 18 includes two camming surfaces 66a, 66b, the portions of the camming surfaces 66a, 66b at a location 90 and 270 degrees, respectively, from the slit 62 are the thinnest and, with rotation of the locking pin 16 in a clockwise or counterclockwise direction, the portions of the camming surfaces 66a, 66b that are in contact with the retention rings 16a, 16b, respectively, increase in thickness. In one variation, the camming surfaces 66a, 66b do not contact the retention rings 16a, 16b at 90 and 270 degrees. As the locking pin 18 rotates through 90 degrees, the thickness of the camming surface 66 increases to contact with the retention ring 16 at the neck 52 and/or at the retention flange 54. Continued rotation of the locking pin 18 results in the camming surface 66 camming against the neck 52 and/or retention flange 54 and moving or deflecting the retention flange 54 inwardly towards the center of the central aperture 48 or towards the central axis of the central aperture 48. In one variation, the camming surface 66 contacts or cams against at least a portion of the undersurface 55 of the retention flange 54 that lies beyond the outside perimeter of the retention ring 16. With continued rotation of the locking pin 18, the camming surface 66 exerts a force on the retention flange 54 flexing the neck 52 inwardly and deflecting the flange 54 inwardly toward the center of the central aperture 48. At the termination of the 90-degree rotation of the locking pin 18, the blocking surface 68 is adjacent to or abuts at least a portion of the retention flange 54 and/or neck 52. In another variation, at the termination of the 90 degree rotation of the locking pin 18, the neck 52 of the retention ring 16 comes into alignment with the slit 62 of the locking pin 18 and is no longer biased or pushed inwardly by the camming surface 66 beyond the unbiased position of the retention flange 54 and neck 52 and therefore, the retention flange 54 is allowed to snap back into its normal position at which point the outer surface 53 of the retention flange 54 is adjacent to or abuts the blocking surface 68 and the blocking surface 68 thereby creating a stop for the retention flange 54 that does not allow the retention flange 54 or neck 52 to flex outwardly and out of the path of fastener 14 that may be backing out. In one variation, the retention flange 54 is deflected inwardly beyond a normal undeflected position to contact and cover at least a portion of the screw head 40. In another variation, the retention flange 54 is deflected inwardly beyond a normal undeflected position to contact, cover and additionally exert a force on at least a portion of the screw head 40 to prevent an inserted bone screw 14 from backing out. The retention flange 54 is maintained in a locked position with the locking pin turned through at least 90 degrees of rotation. In one variation, the snapping back of the retention flange 54 against the blocking surface 68 or into a normal unbiased, undeflected position advantageously provides the surgeon with haptic and/or audible feedback notifying the surgeon that sufficient rotation of the locking pin 18 is achieved and that a locked relationship of the locking pin 18 with the retention ring 16 is established. Rotation of the locking pin 16 in the opposite direction or continued rotation in the same direction will result in the camming surface 66 contacting the retention flange 54 freeing it to flex out of the path of a fastener 14 to achieve an unlocked relationship of the locking pin 18 and retention ring 16 as shown in FIGS. 24 and 25.

In one variation, a portion of the undersurface 55 of the retention flange 54 may have a shape that is complementary to the camming surface 66. In another variation, the portion of the undersurface 55 that lies outside the outer perimeter of the retention ring 16 may be angled or curved to facilitate the camming of the undersurface 55 against the camming surface 66. Also, the portion of the undersurface 55 that lies inside the outer perimeter of the retention ring 16 may be configured to contact and closely cover the bone fastener 14.

The cervical plate system 10 is assembled by first inserting the locking pins 18 into the locking pin apertures 36 located between each pair of through holes 24. The locking pins 18 are secured to the plate 12 such that the locking pins 18 are permitted to move or rotate with respect to the plate 12. An additional coupling mechanism may be employed to connect to the post 60 of the locking pin 18 from the lower surface 22 of the plate 12. Next, the retention rings 16 are inserted into the through holes 24 of the plate 12. As mentioned above, each retention ring 16 is slightly compressible due to the slots 50 formed in the upper surface of the ring 16. The retention rings 16 are compressed and inserted into the through holes 24 and then allowed to expand in the screwhead-receiving portion 26 of the through hole 24 being retained in the through hole 24 by way of a friction fit engagement. Alternatively, as mentioned above, the retention ring 16 may include an annular lip extending radially outwardly and configured to engage with a complementary shaped undercut formed in the plate 12 to connect the retention ring 16 to the plate 12. In yet another variation, the through hole 24 is slightly elliptical in shape that matches a slightly elliptical retention ring 16 which can be inserted in a conforming direction and then rotated into a non-conforming orientation with respect to the through hole 24 to be retained within the through hole 24 by a compression fit engagement. In another variation, the tabs are deflected slightly inwardly towards the central axes upon insertion of the retention ring 16 into a through hole 24 wherein the inwardly deflected tabs advantageously create an undercut for retaining the screw head 40 firmly inside the plate 12 through hole 24. In one variation, the camming surface 66 is sized and configured such that, upon assembly of the plate system 10, at least a portion of the camming surface 66 is positioned underneath the retention flange 54 of the retention ring 16. If a locking pin 18 is configured to lock two adjacent retention rings 16, then at least a portion of both camming surfaces 66a, 66b are positioned underneath or adjacent to the retention flanges 54a, 54b. After the retention rings 16 are inserted into the plate 12, the plate 12 is ready to be implanted into the patient.

Figure 29:
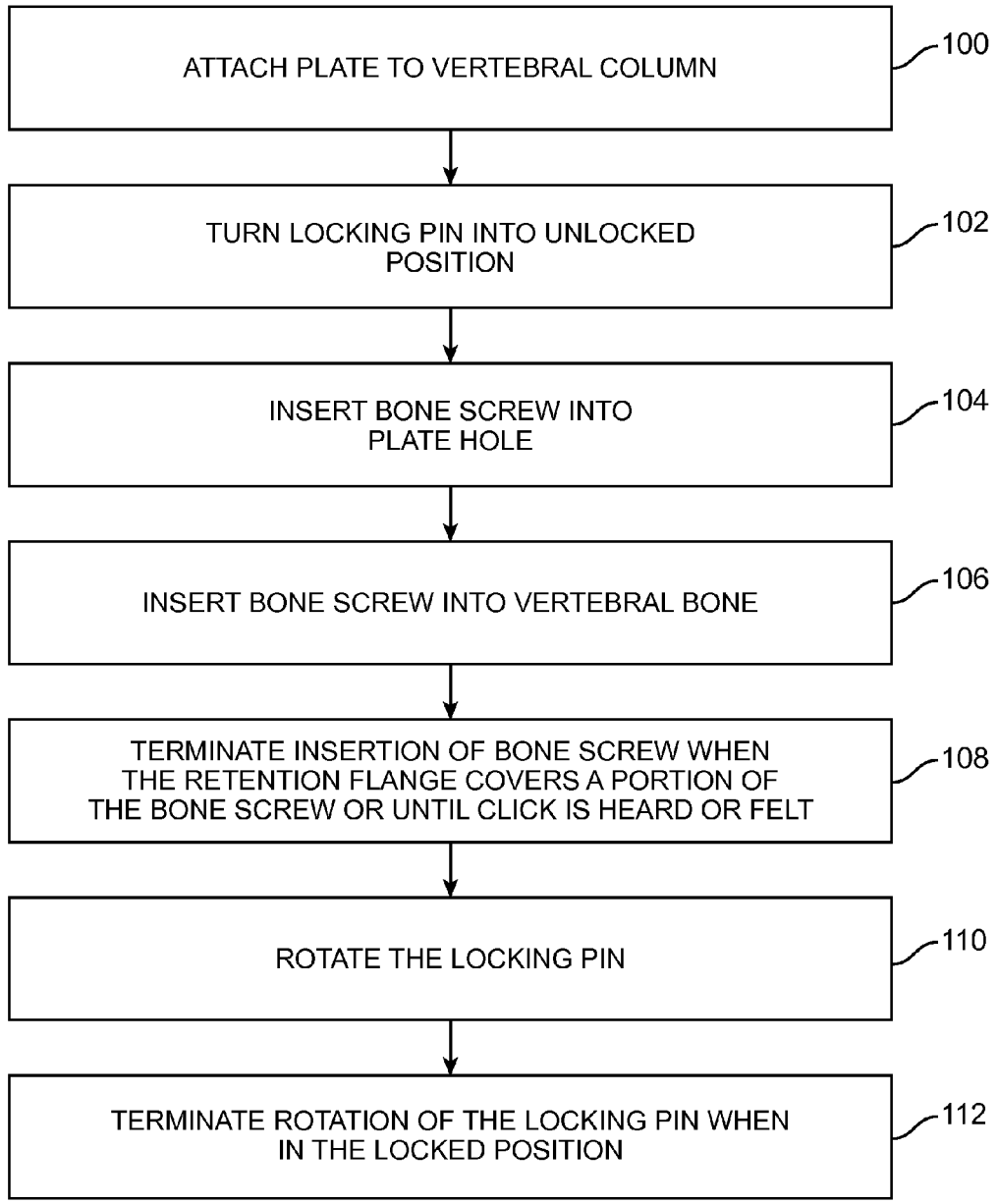
FIG. 29 is a flow chart illustrating a method of securing the cervical plate system according to the present invention to the cervical spine of a patient.

FIG. 29 is a process flow diagram illustrating a method of performing a surgical procedure employing the cervical plate system 10 of the present invention. In step 100, the anterior cervical plate 12 is placed or attached adjacent to a vertebral column. The placement of the plate 12 relative to the vertebral bone in a patient may be pre-operatively determined based on a pre-operative examination of the patient's spine using non-invasive imaging techniques known in the art. Any additional preparation or work may be done on and around the desired vertebrae prior to positioning the plate 12.

Once the plate 12 is appropriately positioned, it may be necessary to turn the locking pins 18 into an unlocked position or check to make sure that they are in an unlocked position in step 102. Next, bone fasteners 14 are inserted into adjacent through holes 24 of the plate 12 in step 104 while the adjacent locking pin 18 is in an unlocked position. To insert a bone fastener 14, an instrument is inserted into the instrument recess 46 of the fastener 12 and the fastener 12 is driven or screwed into the desired bone in step 106. As each bone fastener 14 passes into a through hole 24, it encounters the retention flange 54 and deflects the retention flange 54 outwardly until the head 40 of the fastener 14 or, in particular, the ledge 47 of the screw head 40 has traveled past the retention flange 54. At this point, the retention flange 54 snaps back such that the retention flange 54 partially overlays or covers the fastener head 40. In particular, the retention flange 54 will cover or overlay the fastener ledge 47. The snapping-back of the retention flange 54 onto the fastener head 40 advantageously provides an audible clicking sound or clicking feeling to the surgeon signaling that the fastener 14 is properly seated and need not be driven further into the vertebral bone in step 108. Without this signal to the surgeon, the surgeon may continue to drill the fastener 14 into the bone which may detrimentally affect implantation. Further feedback is provided to the surgeon in that the locking pin 18 cannot be moved into the locked position until and unless at least a portion of the screw head 40 has been fully inserted such that the screw head 40, in particular, the ledge 47 of the screw head 40 is disposed distally of the retention flange 54. The feedback may also be visual as a result of the surgeon observing the position of the retention flange 54 relative to the screw 14 making sure that the retention flange 54 overlays a portion of the screw 14. The retention flange 54 may be colored to enhance visual feedback. Another advantage is that the fastener head 40 is seated in the screwhead-receiving portion 26 of the plate 12 against a slightly compressible retention ring 16. The slightly compressible retention ring 16 advantageously increases purchase of the fastener 14 to the plate 12 by bearing or dampening various anatomical forces imposed onto the fastener 14 instead of directly transmitting such forces undampened to the plate 12 and from the plate 12 to other weaker portions of the vertebral anatomy. Furthermore, the tabs are deflected slightly inwardly towards the central axes upon insertion of the retention ring 16 into a through hole 24 creating a reduced-diameter entry way or undercut for the screw head 40 advantageously covering the screw head 40 in finger-like fashion to retain the screw 14 in place.

Figure 26:
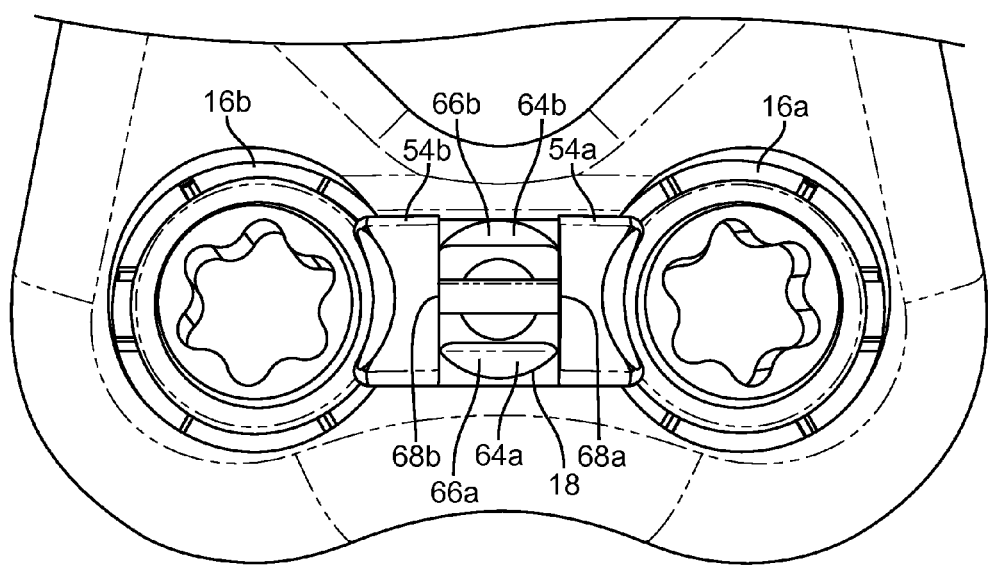
FIG. 26 is a top sectional view of an anterior cervical plate system with a locking pin in a locked position according to the present invention.
Figure 28:
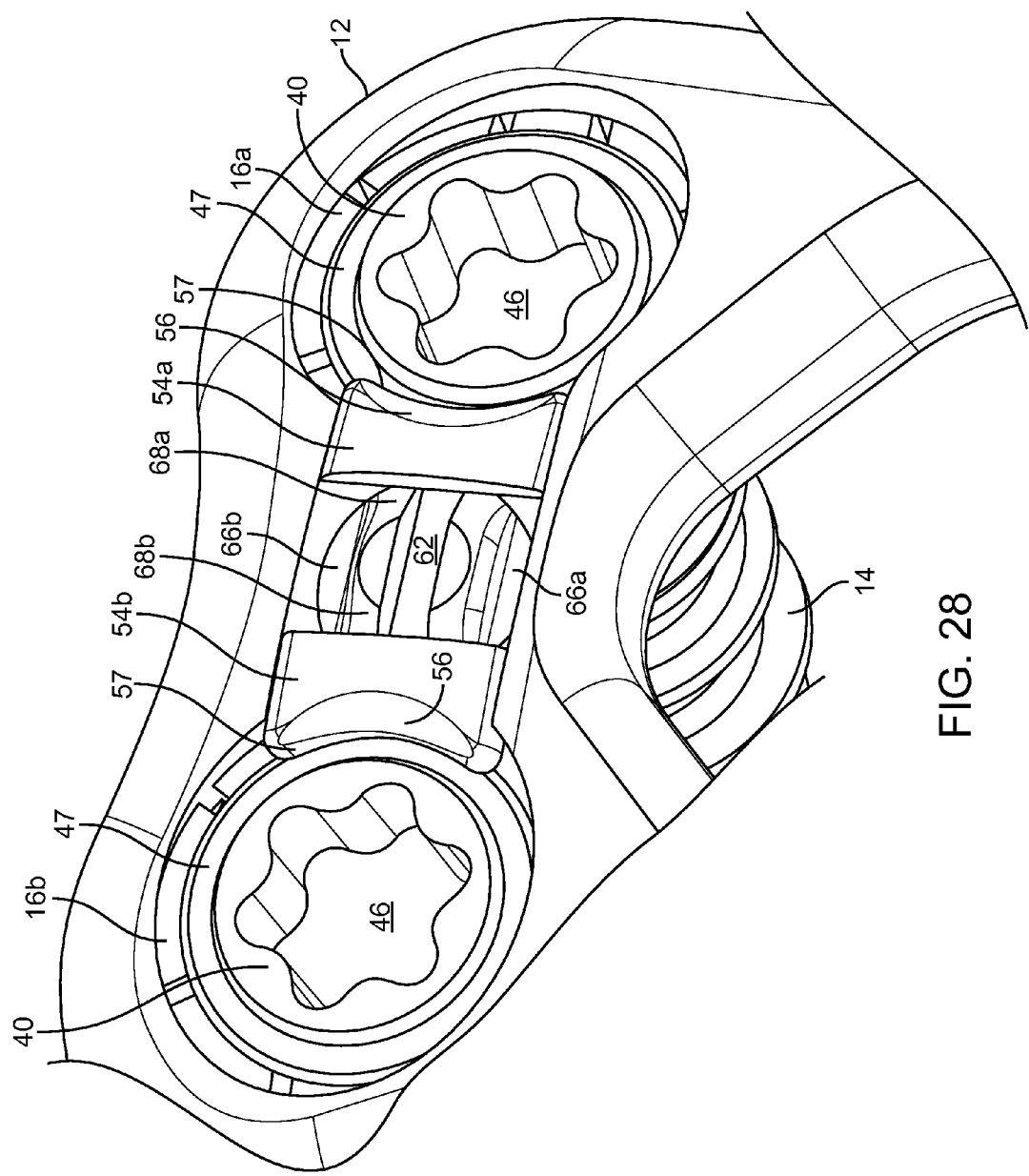
FIG. 28 is a top perspective sectional view of the anterior cervical plate system with a locking pin in a locked position according to the present invention.

Once the fasteners 14 are correctly positioned in the through holes 24, the locking pin 18 is rotated in step 110. To rotate the locking pin 18, an instrument is inserted into the slit 62 or recess of the locking pin 18 and the locking pin 18 is rotated from an unlocked position as shown in FIGS. 24-25 to a locked position as shown in FIGS. 26-28. Rotation of the locking pin 18 is terminated when the blocking surfaces 68a, 68b are adjacent to or abut the adjacent retention flanges 54a, 54b or until a click is heard or felt by the surgeon in step 112. In one variation, the locking pin 18 is rotated 90 degrees from the unlocked position to the locked position, however, the invention is not so limited and the locking pin 18 may be rotated anywhere between approximately 30 degrees and 330 degrees into a locked position. As the locking pin 18 rotates into the locked position, the camming surface 66 deflects the retention flange 54 inwardly toward the center of the retaining ring 16. This inward deflection of the retention flange 54 advantageously displaces any tissue or bone fragments that may interfere with the retention flange 54 effectively covering the bone screw 14. Furthermore, the inward deflection of the retention flange 54 by the blocking surface 68 results in the retention flange 54 contacting and covering at least a portion of the screw head 40 exerting a force onto the screw head 40. This feature advantageously prevents the bone screw 14 from loosening before migrating back out of the through hole 40 and keeps the screw 40 inside the through hole 40. Feedback is provided to the surgeon in that the locking pin 18 cannot be moved into the locked position until and unless the screw head 40 has been fully inserted such that the screw head 40, in particular, the ledge 47 of the screw head 40 is disposed distally of the retention flange 54. The feedback may also be visual, the result of the surgeon observing the position of the locking pin 18 relative to the retention flange 54. The slit 62 may be colored to enhance visual feedback.

To remove the bone plate 12, the same instrument is used to rotate the locking pin 18 from a locked position to an unlocked position in which the blocking surface 68 is not adjacent to or does not abut the retention flange 54 and the retention flange 54 is free to flex outwardly with respect to the retention ring 16. Advantageously, since the instrument recess 46 on the screw head 40 is not blocked by the overlaying retention flange 54, an instrument can be inserted into the instrument recess 46 on the screw head 40 to remove the bone screw 14. Using the instrument to back out the screw 14 results in the screw head 40 camming against the retention flange 54 deflecting it outwardly and out of the pathway of the screw 14 being removed. In another variation, an additional instrument may be employed to keep the retention flange 54 flexed in the outward position while the bone screw 14 is backed out of the bone.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:

1. A bone plate system, comprising:
   a bone screw having a head portion connected to a shank portion;
   a plate having at least one through-hole configured to receive the bone screw for attaching the plate to bone, the through-hole defining an entry and exit pathway for the bone screw;
   a resiliently deflectable retention flange connected to the plate and located in the pathway of the bone screw when in a normal undeflected position,
   wherein the bone screw is configured for insertion into the through-hole past the retention flange such that at least a portion of the head portion is positioned distally of the retention flange, the retention flange having a deflected position permitting insertion of the bone screw into the through-hole; and
   a locking pin being movably connected with respect to the plate, the locking pin having at least one blocking surface,
   wherein the bone plate system includes a locked position in which the blocking surface of the locking pin is in a position adjacent to the retention flange to prevent outward deflection of the retention flange and thereby maintain the retention flange in the pathway of the through-hole and above the bone screw to prevent the bone screw from backing out of the through hole.

2. The bone plate system of claim 1 wherein the bone plate system includes an unlocked position in which the retention flange is deflectable out of the pathway of the bone screw to permit passage of the bone screw into or out of the through-hole.

3. The bone plate system of claim 1 wherein the locking pin further includes at least one camming surface interconnected with the at least one blocking surface, the camming surface being configured to lead into the blocking surface.

4. The bone plate system of claim 3 wherein the bone plate system includes an unlocked position in which the camming surface is located adjacent to the retention flange and the retention flange is deflectable out of the pathway of the bone screw to permit passage of the bone screw into or out of the through-hole.

5. The bone plate system of claim 1 wherein when in the locked position, the blocking surface is configured to deflect the retention flange inwardly toward a center of the through-hole.

6. The bone plate system of claim 1 wherein the retention flange is upwardly spaced from a surface of the plate and located above the through-hole in an undeflected position.

7. The bone plate system of claim 1 wherein the retention flange is integrally formed with a retention ring configured to be disposed inside the at least one through-hole.

8. The bone plate system of claim 1 wherein the retention flange extends radially into an insertion pathway of the bone screw when in a normal undeflected position.

9. A bone plate system, comprising:
   a bone screw having a head portion connected to a shank portion;

a plate having at least one through-hole configured to receive the bone screw for attaching the plate to bone, the through-hole defining an entry and exit pathway for the bone screw;

a resiliently deflectable retention flange connected to the plate and located in the pathway of the bone screw when in a normal undeflected position, wherein the bone screw is configured for insertion into the through-hole past the retention flange such that at least a portion of the head portion is positioned distally of the retention flange, the retention flange being deflectable to permit insertion of the bone screw into the through-hole; and a locking pin connected to the plate and mechanically coupled to at least one adjacent retention flange, the locking pin having at least one blocking surface and at least one camming surface, the locking pin being movable to selectively position the blocking surface and camming surface adjacent to the retention flange, wherein the blocking surface when positioned adjacent to the retention flange is configured to prevent outward deflection of the retention flange to prevent the bone screw from backing out of the through-hole, and the camming surface when positioned adjacent to the retention flange is configured to allow clearance for the retention flange to deflect outwardly to permit the bone screw to pass into and out of the through-hole.

10. The bone plate system of claim 9 wherein the locking pin includes two blocking surfaces oppositely disposed from each other and two camming surfaces oppositely disposed from each other and configured to block or cam two adjacent retention flanges simultaneously.

11. The bone plate system of claim 9 wherein the locking pin is configured to deflect the retention flange toward a center of the through-hole.

12. The bone plate system of claim 9 wherein the locking pin includes a main body, the blocking surface and the camming surface being formed along the perimeter of the main body, wherein the thickness of the main body along the perimeter in the location of the blocking surface is greater than the thickness of the main body along the perimeter in the location of the camming surface.

13. The bone plate system of claim 9 wherein the locking pin defines a circular outer perimeter.

14. The bone plate system of claim 9 wherein the locking pin is configured such that the camming surface and the blocking surface in turn contact at least a portion of the retention flange with movement of the locking pin relative to the plate.

15. A bone plate system, comprising:
a bone screw having a head portion connected to a shank portion;
a plate having at least one through-hole configured to receive the bone screw for attaching the plate to bone, the through-hole defining an entry and exit pathway for the bone screw;
a retention member disposable in the through-hole and including a central aperture having an entry opening at a top surface and a deflectable retention flange upwardly spaced from the top surface, the central aperture adapted to receive the bone screw,
wherein the bone screw is configured for insertion into the through-hole past the retention flange such that at least a portion of the head portion is positioned distally of the retention flange; and
a locking pin being movably connected with respect to the plate, the locking pin having at least one blocking surface,
wherein the bone plate system includes a locked position in which the blocking surface of the locking pin is in a position adjacent to the retention flange to prevent outward deflection of the retention flange and thereby maintain the retention flange in the pathway of the through-hole and above the bone screw to prevent the bone screw from backing out of the through hole.

16. The bone plate system of claim 15 wherein the retention flange extends radially into an insertion pathway of the bone screw when in a normal undeflected position.

17. The bone plate system of claim 15 wherein the retention flange is integrally formed with a retention ring configured to be disposed inside the at least one through-hole.

18. The bone plate system of claim 17 wherein a neck connects the retention flange to the retention ring.

19. The bone plate system of claim 17 wherein the retention ring defines the central aperture adapted to receive the bone screw, the central aperture being smaller than the head portion of the bone screw.

20. The bone plate system of claim 15 wherein when in the locked position, the blocking surface is configured to deflect the retention flange inwardly toward a center of the through-hole.

21. A bone plate system, comprising:
a first bone screw having a head portion connected to a shank portion;
a plate having a first through-hole sized to receive the first bone screw for attaching the plate to bone, the first through-hole defining an entry and exit pathway for the first bone screw;
a first retention member adapted for seating in the first through-hole, the first retention member having a retention flange and an aperture sized to allow passage of the shank but not the head portion of the first bone screw, the retention flange being upwardly spaced from the aperture of the first retention member,
wherein the head portion of the first bone screw is movable past the retention flange so that the retention flange overlies at least a section of the head portion; and
a locking pin being movably connected with respect to the plate, the locking pin having a first blocking surface,
wherein the bone plate system includes a locked position in which the first blocking surface of the locking pin is positionable adjacent to the retention flange to prevent outward deflection of the retention flange and thereby maintain the retention flange in an overlying position above the first bone screw to prevent the first bone screw from backing out of the first through-hole.

22. The bone plate system of claim 21 wherein the retention flange of the first retention member is integrally formed with a retention ring configured to be disposed inside the first through-hole.

23. The bone plate system of claim 22 wherein a neck connects the retention flange to the retention ring of the first retention member.

24. The bone plate system of claim 22 wherein the retention ring of the first retention member includes the aperture sized to permit passage of the shank portion of the first bone screw, but not the head portion.

25. The bone plate system of claim 21 further comprising:
a second bone screw having a head portion connected to a shank portion;

a second through-hole sized to receive the second bone screw for attaching the plate to bone, the second through-hole defining an entry and exit pathway for the second bone screw;

a second retention member adapted for seating in the second through-hole, the second retention member having a retention flange and an aperture sized to allow passage of the shank but not the head portion of the second bone screw, the retention flange being upwardly spaced from the aperture of the second retention member, wherein the head portion of the second bone screw is movable past the retention flange so that the retention flange overlies at least a section of the head portion, and wherein the locking pin includes a second blocking surface and the locked position of the bone plate system is one in which the second blocking surface of the locking pin is positionable adjacent to the retention flange of the second retention member to prevent outward deflection of the retention flange and thereby maintain the retention flange in an overlying position above the second bone screw to prevent the second bone screw from backing out of the second through-hole.

26. The bone plate system of claim 21 wherein the retention flange of the first retention member is resiliently deflectable and extends radially into the pathway of the first bone screw when in a normal undeflected position.

27. The bone plate system of claim 21 wherein when in the locked position, the first blocking surface is configured to deflect the retention flange inwardly toward a center of the first through-hole.

* * * * *